(12) United States Patent
Levinson et al.

(10) Patent No.: US 6,432,084 B1
(45) Date of Patent: Aug. 13, 2002

(54) NON-NEWTONIAN FLUID SPRAY APPLICATOR AND METHOD

(75) Inventors: Mitchell E. Levinson, Pleasanton; Gordon H. Epstein, Fremont, both of CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/566,452

(22) Filed: May 8, 2000

(51) Int. Cl.[7] .................................................. A61M 1/00
(52) U.S. Cl. ....................................................... 604/118
(58) Field of Search ............................. 604/118, 93.01, 604/119, 120, 122; 239/8, 9

(56) References Cited

U.S. PATENT DOCUMENTS

| | | | | |
|---|---|---|---|---|
| 3,594,980 A | * | 7/1971 | Diehl | 261/118 |
| 3,737,106 A | * | 6/1973 | Arnold et al. | 239/513 |
| 3,790,080 A | * | 2/1974 | Babington | 239/422 |
| 3,865,193 A | * | 2/1975 | Hall | 169/65 |
| 3,918,935 A | * | 11/1975 | Livingston | 95/205 |
| 3,991,143 A | * | 11/1976 | Carter | 239/553.3 |
| 4,037,665 A | * | 7/1977 | Hopper | 169/30 |
| 4,191,480 A | * | 3/1980 | Hiorth | 138/42 |
| 4,231,521 A | * | 11/1980 | Hermine | 239/230 |
| 4,236,674 A | * | 12/1980 | Dixon | 239/296 |
| 4,359,049 A | * | 11/1982 | Redl et al. | 604/191 |
| 4,396,417 A | * | 8/1983 | Lissant | 106/243 |
| 4,401,271 A | * | 8/1983 | Hansen | 239/337 |
| 4,401,272 A | * | 8/1983 | Merton et al. | 222/402.24 |
| 4,728,578 A | * | 3/1988 | Higgins et al. | 252/393 |
| 4,928,884 A | * | 5/1990 | Smith | 239/290 |
| RE33,642 E | * | 7/1991 | Lester | 128/200.21 |
| 6,036,103 A | * | 3/2000 | Benest | 239/159 |
| 6,068,203 A | * | 5/2000 | DeYoung et al. | 239/297 |
| 6,183,941 B1 | * | 2/2001 | Hayes | 118/300 |

* cited by examiner

Primary Examiner—Teresa Walberg
Assistant Examiner—Daniel Robinson
(74) Attorney, Agent, or Firm—Oppenheimer Wolff & Donnelly LLP

(57) ABSTRACT

A spray applicator particularly suited to needs of surgeons for dispensing a multi-component fluid, for example fibrin and thrombin components of a tissue adhesive. The spray applicator having a spray nozzle, a liquid dispensing aperture, a spray plate to be impacted by the liquid dispensed and a gas nozzle to provide a stream of carrier gas to carry the dispensed liquid away from the spray plate to form a spray.

14 Claims, 2 Drawing Sheets

COMPARATIVE TEST A: LUMEN 12 HIGH

COMPARATIVE TEST B: LUMEN 12 FORWARD

US 6,432,084 B1

NON-NEWTONIAN FLUID SPRAY APPLICATOR AND METHOD

CROSS-REFERENCE TO RELATED APPLICATIONS

Continuation Status Not Claimed

This application discloses subject matter related to our copending U.S. patent application Ser. Nos. 08/838,078 and 08/839,614 both filed Apr. 14, 1997, to patent application Ser. No. 08/946,364 filed Oct. 7, 1997 and to patent application Ser. No. 09/037,160 filed Mar. 9, 1998, to a patent application Ser. No. 09/302,726 filed Apr. 30, 1999 and entitled "GAS-DRIVEN SPRAYING OF MIXED SEALANT AGENTS" all naming Gordon H. Epstein as first inventor, and to an international PCT patent application in the name of the assignee of all interest of the instant application, Biosurgical Corporation, Application No. PCT/US99/09663 also entitled "GAS-DRIVEN SPRAYING OF MIXED SEALANT AGENTS". The disclosures of the aforementioned United States patent applications, and one international PCT patent application, "the related applications", are hereby incorporated herein by reference thereto. Continuation status is not claimed.

STATEMENT REGARDING FEDERALLY SPONSORED RESEARCH OR DEVELOPMENT (Not applicable.)

BACKGROUND OF THE INVENTION

1. Field of the Invention

The present invention relates to an applicator and method for spray application of a non-Newtonian fluid to a work surface. The invention is particularly, although not exclusively, useful for applying tissue sealant agents containing a polymer such, for example, as fibrinogen, to biological tissue to effect hemostasis or achieve other therapeutic results. More particularly, it relates to spray application of tissue sealants from a hand-held applicator.

2. Description of Related Art Including Information Disclosed under 37 CFR 1.97 and 37 CFR 1.98

Use of tissue sealants and other biological materials is an important emerging surgical technique, well adapted for the operating room or field environments such as the doctor's office or mobile medical units. Preferred sealants include fibrin sealants which are formed from blood plasma components and comprise, on the one hand, a first agent containing fibrinogen and Factor XIII and on the other hand a second agent which usually includes thrombin, and calcium ions. The fibrinogen is capable of a polymerizing and being cross-linked to form a solid fibrin clot when the agents are mixed. The necessary additional factors to simulate relevant portions of the natural blood coagulation cascade are suitably distributed between the fibrinogen and thrombin agents.

High levels of protection against transmission of infections or induction of immunological reactions can be assured by using an autologous or single-donor source for both agents. Such sealants are highly effective, are biologically degraded without residue and may promote wound healing.

They may be dispensed from hand-held applicators which can generally be classified as droplet applicators or spray applicators. Droplet applicators dispense a continuous stream or single line of droplets from a cannula, or other dispensing tube. Spray applicators generate one or more patterns of atomized fluid that can be applied to a work surface so as to cover a wider area than the output from droplet applicators. In many cases the applicators comprise dual syringes providing reservoirs for two sealant agents which are dispensed by manually operated plungers which drive the fluids out of the reservoirs to be mixed internally or externally. Some examples of such applicators, especially ones that address the problems of mixing sealant agents internally, are disclosed in the related applications.

Capozzi et al. U.S. Pat. No. 5,116,315 discloses a spray applicator that outputs a mixture of two sealant agents which applicator is provided with replaceable spray orifices so that when they become clogged with sealant, the user can remove the clogged orifice and replace it with a new one. Changing the clogged orifices is inconvenient and may be difficult and inconvenient during surgery. Fibrin sealants can coagulate very quickly, in a matter of seconds. Accordingly, such a spray applicator can easily become clogged between applications if it is set down for a minute or two. The need to change the spray orifices during a surgical procedure, and to have replacement orifices available, may be quite disruptive or impractical.

Furthermore, the momentum of the spray droplets leaving the applicator is derived from manually applied pressure to the sprayed liquid. Naturally, the pressure with which the liquid is applied to the spray orifice, and therefore the momentum with which the droplets are discharged from the spray orifice, is subject to variation, caused by the mechanics of the dispensing mechanism or simple inability of a human operator to apply constant pressure throughout a range of manual movement. Accordingly with the Capozzi spray applicators, it is difficult to produce an even spray having a consistent spray pattern. It is also difficult to discharge the droplets from the applicator with a constant momentum, as would be desirable for consistent application of materials such as a surgical sealant.

Another approach to this problem has been to entrain the individual sealant agents in separate gas streams, providing overlapping spray patterns, with the intention that the agents will mix in the air or on the tissue surface. Thus, for example, Redl U.S. Pat. No. 4,359,049 discloses a dual syringe tissue adhesive applicator for dispensing two adhesive agents, which applicator employs a disposable mixing needle to provide a mixed sealant output a in the form of a liquid stream or a series of droplets. To provide a spray output, FIGS. 4 and 5 of Redl disclose the use of two pressurized gas streams emerging from outlets 50,51 in the region of the valves 43,44 of conveying channels 41,40 which separately supply adhesive agents from syringe bodies 1 and 2. (See column 3, lines 45–47.) Two spray patterns are generated and, according to Redl "unite at a distance of about 10 to 20 cm, rapidly forming a thin uniform adhesive film on the surface to be adhered or sealed.", see column 4 lines 1–3. As taught in the related application filed Apr. 30, 1999 application Ser. No. 09/302,726, such external mixing of separate sprays provides ineffective mixing and the resultant sealant may lack adhesive or cohesive strength.

Furthermore, depending upon the potency of the particular formulations employed, coagulation of the sealant may take place very rapidly, once the necessary sealant agents are mixed, yielding a gel within perhaps 5 or 20 seconds of mixing. Though often desirable for surgical reasons, such fast-acting properties may aggravate difficulties with atomization, when a mixed sealant is sprayed, and can lead to fouling or clogging of the spray applicator.

Surprisingly, we have found that many known spray applicators exhibit poor spray quality when applying fibrinogen, even spray applicators specifically intended for fibrinogen application, such as those referenced above. Studies we have conducted, pursuant to the present invention, have shown that a fibrinogen agent tends to stream instead of spray when dispensed through conventional spray applicator nozzles, which is wasteful and ineffective. Such drawbacks may render the applicator quite unsuitable for surgical use. The possibility of such streaming is particularly unsatisfactory for many surgical applications where a thin film of sealant is desired. In some cases, thick layers of sealant can be a barrier to the blood supply of connected tissues. To meet the need for a thin layer of deposited sealant, it is desirable for a spray applicator to be capable of generating a consistent, fine spray.

Pursuant to our studies, it appears that because the fibrinogen agent is a polymer solution containing a dissolved long-chain polymer, the fibrinogen molecule, a molecule which has a molecular weight of about 400,000 daltons, the fluid characteristics of the fibrinogen agent may be non-Newtonian. Thus, the viscosity of the fibrinogen agent fluid may vary with shear rate. In particular, the elongational viscosity, which is the resistance of the fluid to being stretched or drawn, increases as the elongational strain rate increases. Consequently, the liquid resists normal atomization forces that are effective to extrude conventional Newtonian fluids, for example water, into thin columns which can quickly break up into a desired fine mist of droplets. Such non-Newtonian properties of fibrinogen solutions or dispersions, attributable to the polymeric character of fibrinogen, renders their behavior unpredictable when subjected to atomizing or nebulizing forces, and may explain why fibrinogen sealants can be difficult to spray.

As taught by Walters in Rheometry (Chapman and Hall Ltd., 1975) at page 25, some non-Newtonian liquids including suspensions of starch, and polymer solutions, exhibit shear-thickening behavior, wherein the viscosity increases with shear rate.

Such systems can display startling phenomena not found in conventional Newtonian liquids. One such phenomenon is the Weissenberg rod-climbing effect wherein certain non-Newtonian liquids subjected to mixing with a rod, may climb up the mixing rod. Lodge in *Elastic Liquids, An Introductory Vector Treatment of Finite-strain Polymer Rheology*, (Academic Press, 1964) describes, at page 242, a die-swell effect where a non-Newtonian extruded through a die may increase in diameter as it leaves the die. Pursuant to the invention disclosed herein, it is apparent that both effects may be of interest to the problem of spraying a sealant comprising a mixture of fibrinogen and an activator such as thrombin, because of the non-Newtonian nature of the fibrinogen component. Since the sealant agents comprising the mixture must be both mixed and sprayed both the rod-climbing and die-swell phenomena may manifest themselves, to hinder the process.

A still further problem arises from an observation reported by Lodge, that atomization of polymer solutions is particularly difficult because they form unusually stable liquid jets, which may extend a considerable distance from the nozzle before surface tension effects cause the jets to break up into separate drops.

Whereas many mathematically derived analytic solutions are available for predicting the fluid behavior of conventional Newtonian fluids, for example water and aqueous solutions of small molecule substances, for polymer solutions, few analytical solutions exist. Henry Green, in *Industrial Rheology and Rheological Structures* (John Wiley & Sons, Inc., 1949) notes that empirical solutions are the only recourse and teaches that when no yield value for an applied stress exists, and the molecules align on flow, then neither Newtonian nor Bingham concepts can be developed into satisfactory instrumental equations. No fundamental concept exists that will define such a material rheologically and lead to a valid instrumental equation of flow. Accordingly, theoretical considerations may explain why there is difficulty in spraying a non-Newtonian fluid, but a offer no help in solving the problem.

Our related patent application filed Apr. 30, 1999 Ser. No. 09/302,726 disclosed and claimed delivery of at least two sealant agents to a gas stream to generate a spray containing the at least two sealant agents but did not address the problems of spraying non-Newtonian fluids. There is accordingly a need for a spray applicator, and method of spraying that will generate a good spray with non-Newtonian fluids such as polymer solutions, and especially with a fibrinogen agent.

SUMMARY OF THE INVENTION

The present invention solves the problem of providing a spray applicator, and method of spraying that are effective with liquids that are difficult to spray, for example non-Newtonian fluids, such as polymer solutions, especially an aqueous fibrinogen agent.

To solve this problem, the invention provides, in one aspect, a spray applicator having a spray nozzle comprising:
   a) a liquid-dispensing aperture providing a source of a liquid to be sprayed;
   b) a spray plate disposed to be impacted by liquid dispensed from the dispensing aperture; and
   c) a gas nozzle to provide a stream of carrier gas;
wherein the carrier gas stream can carry dispensed liquid away from the spray plate to form a spray.

The liquid can be manually dispensed from the dispensing applicator as a jet or stream and wherein the spray plate has an impact surface disposed to intercept the jet or stream. Preferably, the spray plate acts to thin the dispensed liquid and has a shear edge, the carrier gas stream drawing dispensed liquid away from the shear edge.

The spray applicator according to the invention is surprisingly effective in generating a high-quality, fine spray even when the liquid is a non-Newtonian liquid. While the invention is not limited by any particular theory, it appears that the spray plate is effective in converting kinetic energy of the dispensed liquid into a dispersing force and that this dispersing action is augmented by thinning of the liquid on the spray plate and shearing at the shear edge.

In preferred embodiments, the liquid can be an aqueous polymer solution, for example a coagulable sealant, such as a fibrinogen sealant agent, or a mixture of a fibrinogen agent and a thrombin agent.

Optionally, the applicator comprises a suction-applying member extending distally of the spray nozzle and wherein the spray is discharged from the spray nozzle in the direction of the suction-applying member. The suction applying member can prepare the work surface, for example surgical tissue for the application of a sprayed sealant. Also, a preferred embodiment of spray applicator comprises a fibrinogen agent reservoir, a thrombin agent reservoir, a manual actuator to drive the agents from the reservoirs, a dispensing cannula terminating in the liquid dispensing aperture, a mixing chamber to mix the agents and deliver the mixed agents to the dispensing cannula, a suction source and a suction clearing device to apply suction to the mixing chamber and dispensing cannula to clear residual material therefrom.

In another aspect, the invention provides a method of spraying a non-Newtonian liquid comprising manually dispensing the liquid through a dispensing applicator as a jet or a stream, impacting the dispensed liquid on a spray plate and entraining the liquid impacting the spray plate into a gas stream to provide a spray.

Preferably, although not necessarily, the sealant is a biological sealant, for example a tissue adhesive, and the work surface is a biological tissue subject to surgery. The sealant agents can comprise a first, structural agent capable of gelling, and preferably of solidification and a second, activation agent which activates such gelling and, optionally, solidification. More preferably, the sealant is a tissue sealant and the first agent comprises fibrinogen and the second agent comprises, or can generate a fibrinogen activator, especially thrombin or an equivalent thereof.

BRIEF DESCRIPTION OF THE DRAWINGS

One way of carrying out the invention is described in detail below with reference to the drawings which illustrate one or more specific embodiments of the invention and in which.

DESCRIPTION OF THE PREFERRED EMBODIMENTS

Figure 1:
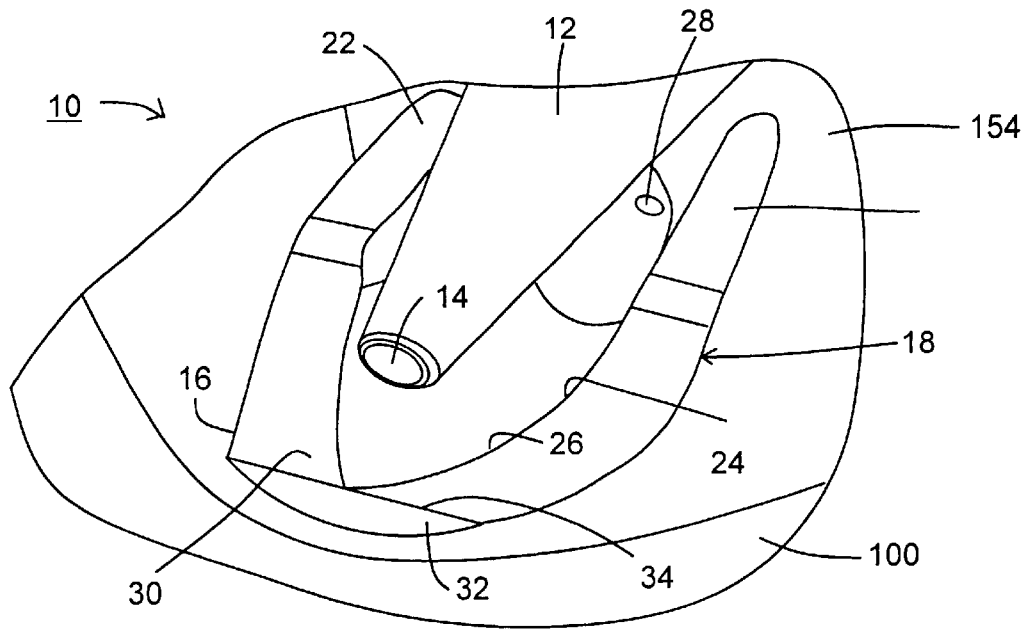
FIG. 1 is a partial perspective view, looking in the proximal direction, of a spray applicator showing details of a spray nozzle according to a preferred embodiment of the invention.
Figure 2:
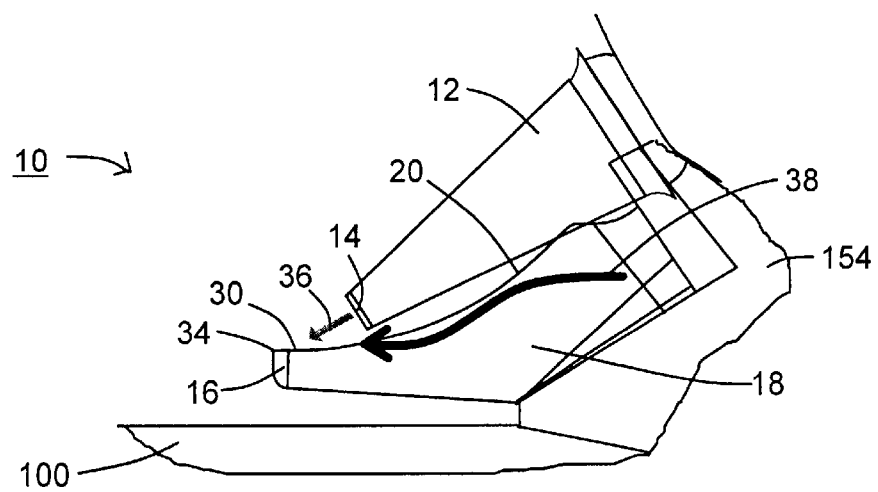
FIG. 2 is a side elevation of the spray applicator shown in FIG. 1.
Figure 3:
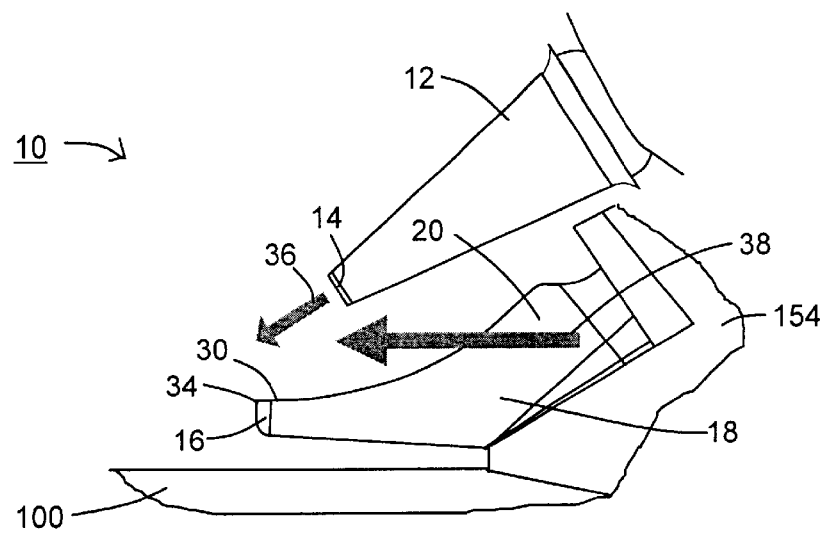
FIG. 3 is a view similar to FIG. 2 of a modified embodiment of spray applicator employed in Comparative Test A.
Figure 4:
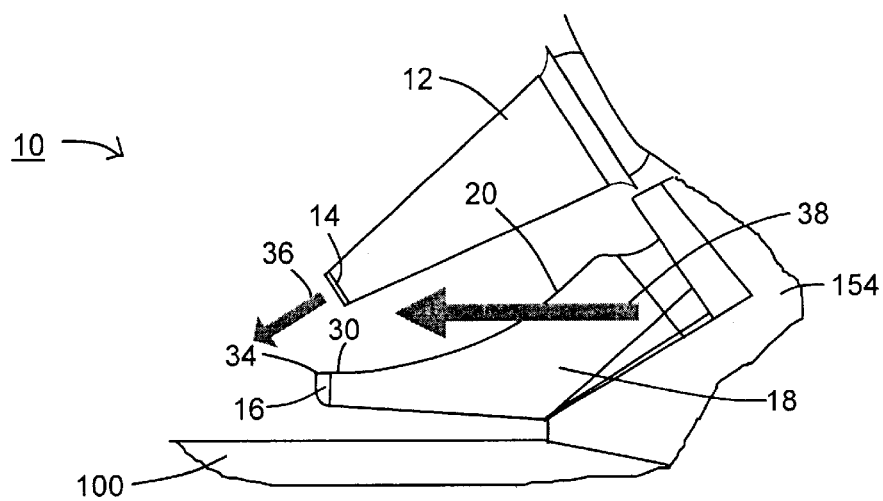
FIG. 4 is a view similar to FIG. 2 of a modified embodiment of spray applicator employed in Comparative Test B.

Referring to FIGS. 1–2, the spray applicator shown may be generally similar to the spray applicator described in related patent application Ser. No. 09/302,726 filed Apr. 30, 1999 and entitled but has a novel spray nozzle 10 of different construction from spray nozzle 106 disclosed in the related application. Accordingly, while spray nozzle 10 is shown in detail, only small portions of the surrounding structure of the spray applicator are shown.

Spray nozzle 10 comprises a dispensing tube or lumen 12 which terminates downwardly in an exit aperture 14 from which a liquid to be sprayed can be dispensed. The dispensed liquid is pressurized, for example by a manually operated mechanical actuator, but not atomized, and is discharged from exit aperture 14 as a jet, a stream or as droplets, of liquid. Because aperture 14 is not intended to generate fine droplets that can be readily airborne (which would be difficult with a non-Newtonian liquid, as explained above) but is, in a preferred embodiment, designed for direct application of mixed fibrinogen sealant agents to surgical tissues, exit aperture 14 is relatively larger in area than would be an atomizing orifice, and any droplets that may be dispensed under relatively low pressure operation will be larger than spray droplets, their size being determined by the area of exit aperture 14. While the invention is not limited to any particular aperture shape or size, exit aperture 14 preferably is circular and has a diameter in the range of about 0.25 to about 2.5 mm (about 0.01 to about 0.1 in.), more preferably about 0.5 to about 1.5 mm (about 0.02 to about 0.6 in.), with one suitable size being about 0.75 mm (0.03 in.) in diameter.

The spray liquid can be any liquid suitable for spraying but is preferably a non-Newtonian liquid, for example, fibrinogen or other polymer solution, or other sprayable aqueous or non-aqueous liquid sealant material, or a non-Newtonian paint or the like.

A spray plate 16 is oriented and disposed under lumen 12 to stop or deflect the dispensed liquid. It will be understood that lumen 12 could be lumen 18 or lumen 124, as described in related application Ser. No. 09/302,726. A gas nozzle 18 incorporating spray plate 16 at its distal edge, is disposed beneath lumen 12 and has a cut away mouth 20 defined by set back shoulders 22, which embrace and support lumen 12. Gas nozzle 18 has a hollowed-out interior 24 with a proximally tapering groove 26 in the floor of interior 24 which leads distally to spray plate 16. A gas orifice 28 is disposed in gas nozzle 18, proximally upstream of spray plate 16, and provides a stream of carrier gas, for example air, which is guided by nozzle interior 24 toward spray plate 16. The kinetic energy of the air atomizes the stream of liquid such as a fibrin sealant and conveys the spray onto the target work surface, for example surgical tissue.

Spray nozzle 10 of the invention is shown, for exemplary purposes, mounted in an spray tip assembly such as taught in the Ser. No. 09/302,726 application as suggested by the partial showing of suction nose 100 and cowling 154. Other spray applicators in which spray nozzle 10 may usefully be employed will be apparent to those skilled in the art.

Spray plate 16 comprises an impact surface 30 to be impacted by liquid discharged from lumen 12, and is preferably constructed as a shear plate with a proximal face 32 at a relatively large acute angle to impact surface 30, or approximately perpendicular thereto, and with a sharp shear edge 34 defined where impact surface 30 and face 32 meet. Arrows 36 and 38 schematically indicate the flow of liquid dispensed from lumen 12 and of the gas stream emerging from gas orifice 28, respectively. As shown in FIG. 2, arrow 36, indicating liquid flow from lumen 12 is directed toward impact surface 30 of spray plate 16, while arrow 38 suggests the gas stream is deflected downwardly by lumen 12. In practice, the area of impact on spray plate 16 may vary, depending upon the velocity with which the spray liquid is discharged from lumen 12 and the velocity of the gas stream, but it appears preferable that lumen 12 and spray plate 16 be aligned for most of the liquid from lumen 12 to strike impact surface 30 just behind shear edge 34.

Liquid arriving at surface 30 is carried off distally by the gas stream, forming a good spray, even when employing a fibrinogen sealant mixture having the difficult non-Newtonian properties described herein.

While the invention is not bound by any particular theory, it appears that impact surface 30 acts as a stop for the liquid agent coming out of lumen 12, deflecting the flow and permitting some of the kinetic energy of the liquid to be used to facilitate dispersion into droplets. Impact surface 30 also prevents the liquid passing right through the gas stream, as might occur were no impact surface aligned with lumen 12. In such a case the user would need to dispense liquid relatively slowly to avoid "shoot-through". As shown in FIG. 2, the provision of spray plate 16 with impact surface 30, renders the design relatively insensitive to application rate, which is operator-dependent and difficult to control.

Additionally, it appears that impact surface 30 is valuable in providing a surface on which the intercepted liquid stream can spread out. Such thinning of the liquid agent attributable to wetting of surface 30 and the pressure of the fluid hitting the surface, make the liquid easier to atomize.

Furthermore, as the gas stream draws the liquid off spray plate 16, the liquid shears off sharp edge 34 aiding atomization. Also it appears that with the juxtaposition of lumen 12 and gas nozzle 18 shown in FIG. 2, the airflow pattern under the application lumen probably is such that the air is constricted by the application lumen enhancing entrainment.

The cut away configuration of the device provided by set back shoulders 22 is valuable in providing a user with full visibility of the tip 31 of lumen 12, and also for providing access thereto, to remove clogs, if necessary. Thus, for example, inadvertent discharge of a coagulable material, such as sealant, which sets up in aperture 14 and has an external portion that cannot be removed by retrograde suction, may be removed manually, if desired. In an alternative construction, gas nozzle 18 has a cup-like configuration, similar to spray nozzle 106 of related application, with lumen 12 discharging sealant against an inside wall portion of spray nozzle 106. However, such alternative construction lacks the advantages of visibility and accessibility provided by the embodiment of FIGS. 1 and 2.

While lumen aperture 14 is shown disposed within the gas stream it could be disposed outside the gas stream, and discharge liquid into the gas stream to hit impact surface 30. Similarly, spray plate 16, or the output from spray plate 16, could be disposed outside the gas stream, and the gas stream could be disposed to entrain the fluid droplets exiting from spray plate 16.

In summary, the described spray applicator is particularly useful for atomizing macromolecular fluids, for example sealants, including fibrin sealants whose dynamic rheology impedes atomization. Significant forces acting at the spray plate acting positively on the cohesive, aligned large molecules of the sealant or other shear-thickening liquid help divide the liquid into fine particles for dispersion. Other liquids that may be beneficially sprayed, employing such a gas-driven shear-spray applicator, for example paints, coatings and the like, will be apparent to those skilled in the art.

As will be apparent to those skilled in the art, spray nozzle 10 can, with only minor modifications or adaptations, such as may be necessary, be substituted for spray nose 106 in the preferred embodiment of the invention shown and described in related patent application Ser. No. 09/302,726 filed Apr. 30, 1999

The performance of the spray applicator of the invention is determined in a test employing a spray applicator substantially as described and shown in FIGS. 8–34 of related patent application Ser. No. 09/302,726 filed Apr. 30, 1999. with the use of a spray nozzle as described with reference to FIGS. 1 and 2 (Test 1) and with a spray nozzle similar to spray nozzle 106 of the Ser. No. 09/302,726 with a cup-like spray body 172, except that the lumen 124 is positioned to direct liquid at the bottom inside surface of spray body 172. The dispensed liquid comprises a mixed fibrin sealant obtained from a fibrinogen agent stored in one syringe of the applicator and a thrombin agent stored in the other syringe of the applicator. In both Test and Test 2, good quality sprays are generated, notwithstanding the difficult nature of fibrinogen. The embodiment used in Test 1 provides the advantages of visibility and accessibility.

Comparative tests A and B are conducted employing different relative positions of dispensing lumen 12 and impact surface 30 as shown in FIGS. 3 and 4. In Comparative Test A, lumen 12 is relatively high, sufficiently far above gas nozzle 18 that liquid dispensed from aperture 14 traveling in the direction of arrow 36 misses impact surface 30. The test shows that this configuration can generate a good spray at relatively low application rates, which is to say liquid discharge rates, that may be difficult for an operator to set. However, when the application rate is relatively high, as it often is, much of the fibrin liquid passed right through the air stream, and landed on spray nose 100 instead of on the target, impact surface 30. Also, the spray quality is not as fine as in Tests 1 and 2. As the fibrin leaves the application lumen 12, it shears off the end of the lumen, and some of the droplets are larger than may be desirable.

Similarly, Comparative Test B shows that moving the application lumen 12 forward is also unsatisfactory at higher application rates because there is no impact surface under lumen 12 to stop the liquid from passing through the air stream as shown in FIG. 4.

Related application Ser. No. 09/037,160 discloses various sealant applicators comprising an applicator body provided with a pair of syringe reservoirs, for two liquid sealant agents, which agents are dispelled from the syringe reservoirs by manual pressure applied to a trigger-like actuator. The body also is fitted with a suction connection and manually operable suction control valve. A range of applicator heads or tips is mountable on to the applicator body to provide selected functionality. A mixing tip (or head) enables the two liquid agents to be discharged into a mixing chamber where they are thoroughly mixed, and provides a flow of mixed sealant to lumen 12 of FIG. 1 herewith.

A preferred mixing tip also enables the operator to terminate sealant flow and apply suction to the dispensing lumen to clear it of polymerized sealant and debris. The technique may be termed "retrograde" clearing. The sealant dispensing pathway can be appropriately configured, with a non-diminishing cross-section in the clearing direction, to facilitate such clearing. Such an applicator, provided with a mixing tip and suction clearing, is preferred in the practice of the present invention to deliver sealant to lumen 12 which would be a component of such a sealant applicator.

While illustrative embodiments of the invention have been described above, it is, of course, understood that various modifications will be apparent to those of ordinary skill in the art. Many such modifications are contemplated as being within the spirit and scope of the invention.

What is claimed is:

1. A spray applicator having a spray nozzle comprising:

a) a liquid-dispensing aperture providing a source of a liquid to be sprayed;

b) a spray plate disposed to be impacted by liquid dispensed from the dispensing aperture; and c) a gas nozzle to provide a stream of carrier gas;

wherein the carrier gas stream can carry dispensed liquid away from the spray plate to form a spray.

2. A spray applicator according to claim 1 wherein the liquid can be manually dispensed from the dispensing applicator as a jet or stream and wherein the spray plate has an impact surface disposed to intercept the jet or stream.

3. A spray applicator according to claim 2 wherein the spray plate acts to thin the dispensed liquid.

4. A spray applicator according to claim 2 wherein the spray plate has a shear edge and the carrier gas stream draws dispensed liquid away from the shear edge.

5. A spray applicator according to claim 1 wherein the liquid is a non-Newtonian liquid.

6. A spray applicator according to claim 5 wherein the liquid is an aqueous polymer solution.

7. A spray applicator according to claim 1 wherein the liquid comprises a coagulable sealant.

8. A spray applicator according to claim 1 wherein the liquid comprises a fibrinogen sealant agent.

9. A spray applicator according to claim 1 wherein the liquid the liquid is a fibrin sealant and comprises a mixture of a fibrinogen agent and a thrombin agent.

10. A spray applicator according to claim 1 the applicator comprises a suction-applying member extending distally of the spray nozzle and wherein the spray is discharged from the spray nozzle in the direction of the suction-applying member.

11. A spray applicator according to claim 10 wherein the applicator comprises a fibrinogen agent reservoir, a thrombin agent reservoir, a manual actuator to drive the agents from the reservoirs, a dispensing cannula terminating in the liquid dispensing aperture, a mixing chamber to mix the agents and deliver the mixed agents to the dispensing cannula, a suction source and a suction clearing device to apply suction to the mixing chamber and dispensing cannula to clear residual material therefrom.

12. A device according to claim 1 wherein the liquid or other material to be dispensed is discharged under pressure, from a lumen terminating in the dispensing aperture, toward and onto the spray plate across a gap through which the gas stream can flow.

13. A device according to claim 1 wherein the lumen is oriented so that the direction of fluid discharge has a significant component in the direction of gas flow.

14. A method of spraying a non-Newtonian liquid comprising manually dispensing the liquid through a dispensing applicator as a jet or a stream, impacting the dispensed liquid on a spray plate and entraining the liquid impacting the spray plate into a gas stream to provide a spray.

* * * * *

UNITED STATES PATENT AND TRADEMARK OFFICE
CERTIFICATE OF CORRECTION

PATENT NO.   : 6,432,084 B1
DATED        : August 13, 2002
INVENTOR(S)  : Mitchell E. Levinson and Gordon H. Epstein It is certified that error appears in the above-identified patent and that said Letters Patent is hereby corrected as shown below:

<u>Title page,</u>
Item [22], the correct filing date of the patent is as follows:
-- Filed: May 5, 2000 --

Insert:
-- Related U.S. Application Data
[60] Provisional application No. 60/133,165, filed on May 7, 1999 --

Signed and Sealed this

Seventeenth Day of February, 2004

JON W. DUDAS
*Acting Director of the United States Patent and Trademark Office*